(12) United States Patent
Bhogal et al.

(10) Patent No.: US 10,456,344 B2
(45) Date of Patent: Oct. 29, 2019

(54) HAIR COMPOSITION (71) Applicant: Conopco, Inc., Englewood Cliffs, NJ (US)

(72) Inventors: Ranjit Kaur Bhogal, Huntingdon (GB); Gail Jenkins, Huntingdon (GB); Magdalena Sawicka, Bedford (GB); Linda Jane Wainwright, Perry (GB)

(73) Assignee: CONOPCO, INC., Englewood Cliffs, NJ (US)

( * ) Notice: Subject to any disclaimer, the term of this patent is extended or adjusted under 35 U.S.C. 154(b) by 0 days.

(21) Appl. No.: 15/533,757

(22) PCT Filed: Dec. 4, 2015

(86) PCT No.: PCT/EP2015/078709
§ 371 (c)(1),
(2) Date: Jun. 7, 2017

(87) PCT Pub. No.: WO2016/102177
PCT Pub. Date: Jun. 30, 2016

(65) Prior Publication Data
US 2017/0360673 A1    Dec. 21, 2017

(30) Foreign Application Priority Data

Dec. 22, 2014 (EP) .................................. 14199852

(51) Int. Cl.
| | | |
|---|---|---|
| *A61K 8/63* | (2006.01) | |
| *A61K 8/46* | (2006.01) | |
| *A61K 8/42* | (2006.01) | |
| *A61K 8/49* | (2006.01) | |
| *A61K 36/88* | (2006.01) | |
| *A61Q 17/00* | (2006.01) | |
| *A61K 8/97* | (2017.01) | |
| *A61K 31/56* | (2006.01) | |
| *A61K 31/575* | (2006.01) | |
| *A61K 36/04* | (2006.01) | |
| *A61K 36/15* | (2006.01) | |
| *A61K 36/185* | (2006.01) | |
| *A61K 36/324* | (2006.01) | |
| *A61K 36/328* | (2006.01) | |
| *A61K 36/68* | (2006.01) | |
| *A61K 36/73* | (2006.01) | |
| *A61Q 7/00* | (2006.01) | |

(52) U.S. Cl.
CPC .................. *A61K 8/63* (2013.01); *A61K 8/42* (2013.01); *A61K 8/46* (2013.01); *A61K 8/498* (2013.01); *A61K 8/4973* (2013.01); *A61K 8/97* (2013.01); *A61K 31/56* (2013.01); *A61K 31/575* (2013.01); *A61K 36/04* (2013.01); *A61K 36/15* (2013.01); *A61K 36/185* (2013.01); *A61K 36/324* (2013.01); *A61K 36/328* (2013.01); *A61K 36/68* (2013.01); *A61K 36/73* (2013.01); *A61K 36/88* (2013.01); *A61Q 7/00* (2013.01); *A61Q 17/00* (2013.01); *A61K 2800/592* (2013.01); *A61K 2800/70* (2013.01)

(58) Field of Classification Search
CPC ........ A61K 31/56; A61K 31/575; A61K 8/42; A61K 8/46; A61K 8/49; A61K 8/63
See application file for complete search history.

(56) References Cited

U.S. PATENT DOCUMENTS

| | | |
|---|---|---|
| 4,009,256 A | 2/1977 | Nowak, Jr. et al. |
| 5,543,074 A | 8/1996 | Hague |
| (Continued) | | |

FOREIGN PATENT DOCUMENTS

| | | |
|---|---|---|
| CA | 2701378 | 10/2011 |
| CN | 102093459 | 6/2011 |
| (Continued) | | |

OTHER PUBLICATIONS

All-in-one nutrient formula dietary supplement, Mintel GNPD Database, 2011, pp. 1-7; XP002741682; Accession No. 1631948 (NPL 1, pp. 1-7).

(Continued)

*Primary Examiner* — Zohreh A Fay
(74) *Attorney, Agent, or Firm* — Foley & Lardner LLP (57) ABSTRACT

Disclosed is an oral or topical composition comprising a nuclear factor erythroid-2 related factor 2 agonist and a liver X receptor agonist, wherein the amounts of each of the nuclear factor erythroid-2 related factor 2 agonist and the liver X receptor agonist produce a synergistic benefit of hair fiber growth, wherein the oral or topical composition comprises ≤9, preferably ≤8% w/w β-sitosterol, wherein when the oral or topical composition comprises a catechin, the oral or topical composition comprises 0.001 to 90, preferably 0.005 to 70, most preferably 0.01 to 50% w/w catechins, wherein the oral or topical composition excludes pregnenolone, 4, 5-dihydrofuranodiene-6-one, epoxy santamarin, hydroquinone, longistyline, monacolin K, protoanemonin, N-(2,2,2-tri-fluoro-ethyl)-N-[4-(2,2,2-tri-fluoro-1-hydroxy-1-trifluoromethyl-ethyl)-phenyl]-benzenesulfonamide, dihydronepetalactone, iridomyrmecin, and dihydroactinidiolide, wherein when the oral or topical composition comprises guggelsterone and epigallocatechin gallate, the oral or topical composition excludes a guggelsterone to epigallocatechin gallate weight ratio of 1 to 28, and wherein when the oral or topical composition comprises sodium dilauramide glutamide lysine, the oral or topical composition excludes 0.3% w/w sodium dilauramide glutamide lysine.

10 Claims, 1 Drawing Sheet

(56) References Cited

U.S. PATENT DOCUMENTS

| | | |
|---|---|---|
| 7,744,931 B2 | 6/2010 | Newmark et al. |
| 8,343,517 B1 | 1/2013 | Bezzek |
| 2003/0027772 A1 | 2/2003 | Breton et al. |
| 2003/0153541 A1 | 8/2003 | Dudley et al. |
| 2005/0013871 A1 | 1/2005 | Niazi et al. |
| 2005/0260285 A1 | 11/2005 | DiMateeo-Leggio |
| 2006/0121103 A1 | 6/2006 | Kirby et al. |
| 2007/0254026 A1 | 11/2007 | Stewart et al. |
| 2007/0292493 A1 | 12/2007 | Brierre |
| 2008/0044390 A1 | 2/2008 | Jin et al. |
| 2008/0069779 A1 | 3/2008 | Tamarkin et al. |
| 2008/0254055 A1 | 10/2008 | Oblong et al. |
| 2010/0159079 A1 | 6/2010 | Qvyjt |
| 2010/0172964 A1 | 7/2010 | Akatsuka et al. |
| 2010/0197795 A1 | 8/2010 | Bettle, III et al. |
| 2010/0240628 A1 | 9/2010 | Jenkins et al. |
| 2011/0003841 A1 | 1/2011 | Shukla |
| 2011/0052754 A1 | 3/2011 | Foley |
| 2011/0318405 A1 | 12/2011 | Erwin |
| 2012/0082739 A1 | 4/2012 | Ghorbani |
| 2013/0034537 A1 | 2/2013 | Gocan et al. |
| 2014/0023721 A1 | 1/2014 | Amelotti |
| 2014/0212388 A1 | 7/2014 | Prieto |

FOREIGN PATENT DOCUMENTS

| | | |
|---|---|---|
| CN | 102920755 | 2/2013 |
| CN | 103977110 | 8/2014 |
| EP | 1994923 | 11/2008 |
| EP | 2295595 | 3/2011 |
| EP | 2114363 | 12/2013 |
| FR | 2888725 | 1/2007 |
| JP | 2001039849 | 2/2001 |
| JP | 2012171893 | 2/2001 |
| KR | 100818175 | 4/2008 |
| KR | 20090005479 | 1/2009 |
| WO | WO9907381 | 2/1999 |
| WO | WO0166560 | 9/2001 |
| WO | WO0205776 | 1/2002 |
| WO | WO2004078157 | 9/2004 |
| WO | WO2005041996 | 5/2005 |
| WO | WO2005058314 | 6/2005 |
| WO | WO2006017211 | 2/2006 |
| WO | WO2008139264 | 11/2008 |
| WO | WO2009105234 | 8/2009 |
| WO | WO2011080579 | 7/2011 |
| WO | WO2013149323 | 10/2013 |
| WO | WO2014008366 | 1/2014 |
| WO | WO2014025905 | 2/2014 |
| WO | WO2014095289 | 6/2014 |
| WO | WO2014168736 | 10/2014 |
| WO | WO2014186395 | 11/2014 |
| WO | WO2015043907 | 4/2015 |

OTHER PUBLICATIONS

Anti-Aging Scalp Serum, Mintel GNPD Database, 2013, XP-002741681; Accession No. 2151342 (NPL 1, pp. 8-12).
Nourishing Scalp Conditioner, Mintel GNPD Database, 2013, XP-002741680; Accession No. 2151386 (NPL 1, pp. 13-17).
Arck et al., Towards a "free radical theory of graying"—melanocyte apoptosis in the aging human hair follicle is an indicator of oxidative stress induced tissue damage, FASEB J, Jan. 1, 2006, pp. 1567-1569, vol. 2, GB (NPL 1, pp. 18-20).
Chase, Growth of the Hair, Physiol Rev, Jan. 1, 1954, pp. 113-126, vol. 34, US (NPL 1, pp. 15-35).
Dhurat et al., Loose Anagen Hair Syndrome, Int J Trichology, Jul. 1, 2010, pp. 96-100, vol. 2, No. 2, EP (NPL 1, pp. 36-43).
Dry, The Coat of the Mouse (Mus Musculus), J Genet, 1926, pp. 281-340, 16, GB (NPL 1, pp. 44-101).
Hybertson, Oxidative stress in health and disease—The therapeutic potential of Nrf2 activation, Molecular Aspects of Medicine, Jan. 1, 2011, pp. 234-246, vol. 32, US (NPL 2, pp. 1-13).
IPRP2 in PCTEP2015078709, Apr. 24, 2017 (NPL 2, pp. 14-30).
Itoh, An Nrf2/Small Maf Heterodimer Mediates the Induction of Phase II Detoxifying Enzyme Genes through Antioxidant Response Elements, Biochemical and Biophysical Research Communications, Jul. 1, 1997, pp. 313-322, vol. 236, JP (NPL 2, pp. 31-40).
Itoh, Keap1 represses nuclear activation of antioxidant responsive elements by Nrf2 through binding to the amino-terminal Neh2 domain, Genes Dev, Jan. 1, 1999, pp. 76-86, vol. 13, No. 1, JP (NPL 2, pp. 41-52).
Kligman, The Human Hair Cycle, Journal Invest Dermatol, Apr. 18, 1959, pp. 307-316, 33, US (NPL 2, pp. 53-62).
Kobayashi, Oxidative Stress Sensor Keap1 Functions as an Adaptor for Cul3-Based E3 Ligase to Regulate Proteasomal Degradation of Nrf2, Mol Cell Biol, Aug. 1, 2004, pp. 7130-7139, vol. 24, No. 16, JP (NPL 2, pp. 63-72).
Lee, An Important Role of Nrf2-ARE Pathway in the Cellular Defense Mechanism, Journal of Biochem & Mol Biol, Mar. 1, 2004, pp. 139-143, vol. 37, No. 2, US (NPL 2, pp. 73-77).
Leung et al., Encyclopedia of common and natural ingredients used in food, drugs and cosmetics, Encyclopedia of Common Natural Ingredients Used in Food, Drugs and Cosmetics, 1996, pp. 36, 38, 68; XP002373460 (NPL 2, pp. 78-95).
Lu, Profiling the Response of Human Hair Follicles to Ultraviolet Radiation, Journal of Investigative Dermatology Jan. 1, 2009, pp. 1790-1804, vol. 129, DE (NPL 3, pp. 1-15).
Moi, Isolation of NF-E2-related factor 2 (Nrf2), a NF-E2-like basic leucine zipper transcriptional activator that binds to the tandem NF-E2-AP1 repeat of the B-globin locus control region, Proc Natl Acad Sci, Oct. 1, 1994, pp. 9926-9930, vol. 91, Issue 21, US (NPL 3, 16-20).
Mundada et al., Pharmacology of Tridax procumbens a Weed: Review, International Journal of Pharmtech Research, 2010, pp. 1391-1394; XP055198747, vol. 2, No. 2 (NPL 3, pp. 21-24).
Philpott et al., Human hair growth in vitro, J Cell Sci, Jan. 1, 1990, pp. 463-471, vol. 97, GB (NPL 3, pp. 24-34).
Sawant and Godghate, Preliminary Phytochemical Analysis of Leaves of Tridax Procumbens Linn, Intl Journal of Science, Jan. 1, 2013, pp. 388-394, vol. 2, No. 3, IN (NPL 3, pp. 35-41).
Search Report & Written Opinion in PCTEP2015078709, dated Feb. 8, 2016 (NPL 3, pp. 42-59).
Search Report in EP14199852, dated Jul. 22, 2015, EP (NPL 3, 60-64).
Sekhar, Cysteine-based regulation of the CUL3 adaptor protein Keap1, Toxicology and Applied Pharmacology, Jun. 1, 2009, pp. 21-26, vol. 244, US (NPL 3, pp. 65-70).
Taylor, Technical Data Report for Cat's Claw, Internet Citation, 2005, pp. 1-38; XP003000971; http://www.rain-tree.com/catsclawtechreport.pdf (NPL 4, pp. 1-38).
Written Opinion in EP14199852, dated Jul. 22, 2015, EP (NPL 4, pp. 39-44).
Written Opinion in PCTEP2015078709, dated Mar. 16, 2017 (NPL 4, pp. 45-55).
Yamamoto, Physiological Significance of Reactive Cysteine Residues at Keap1 in Determining Nrf2 Activity, Molecular and Cellular Biology, Apr. 1, 2008, pp. 2758-2770, vol. 28, No. 8, JP (NPL 4, pp. 56-68).
Kay et al.; Nrf2 Inhibits LXRα-Dependent Hepatic Lipogenesis by Competing with FXR for Acetylase Binding; Antioxidants & Redox signaling; 2011; pp. 2135-2146; vol. 15, No. 8.
Yang et al.; Lycopene and the LXRα agonist T0901317 synergistically inhibit the proliferation of; Journal of Nutritional Biochemistr; 2012; pp. 1155-1162; 23.
Wang et al.; Chemical constituents from traditional Chinese medicine; Zhongguo Zhong Yao Za Zhi; 2014; 2 pages (English abstract only); 39 (24).
Zagreb et al.; A rapid profiling of hypolipidemic agents in dietary supplements; Journal of Food Composition and Analysis; 2014; pp. 68-74; vol. 34.
Liu et al.; Chemical constituents from leaves of Cajanus cajan; Chinese Traditional and Herbal Drugs; 2014; pp. 466-470 (English abstract and original); 45(4).

(56) References Cited

OTHER PUBLICATIONS

Ding et al.; Studies on chemical constituents from root of Actinidia; Zhongguou Zhong Yao Za Zhi; 2007; pp. 1893-5 (2 pages in total, English Abstract only); 32(18).
Anarthe et al.; Evaluation of Polyherbal Formulations of some traditional medicinal Plants for hair growth promoting activity; INDO American Journal of Pharmaceutical Research; 2014; pp. 1526-1529; vol. 4, issue 3.
Cho et al.; Nrf2-regulated PPARγ Expression Is Critical; Am J Respir Crit Care Med; 2010; pp. 170-182; 182.
Chorley et al.; Identification of novel NRF2-regulated genes by ChIP-Seq: influence on retinoid X receptor alpha; Nucleic Acids Research ; 2012; pp. 1-14.
Jung et al.; n-3 Fatty acids ameliorate hepatic steatosis and dysfunction after LXR agonist ingestion in mice; Biochimica et Biophysica Acta 1811; 2011; pp. 491-497.
Kakumu et al.; Phytochemical analysis and antileukemic activity of polyphenolic; Bioorganic & Medicinal Chemistry Letters; 2014; pp. 4286-4290; 24.
Polvani et al.; PPARγ and Oxidative Stress: Con(β) Catenating NRF2 and FOXO; PPAR Research; 2012; pp. 1-16.
Poon et al.; Regulatory mechanism of Toona sinensis on mouse leydig cell steroidogenesis; Life Sciences; 2005; pp. 1473-1487.
Yoshikawa et al.; Response Elements X Receptor (LXR) Binding to LXR 1c Promoter Activity by Inhibition of Liver Sterol Regulatory Element-binding Protein; The Journal of Biological Chemisty; 2002; pp. 1705-1711; 227.
Wang et al.; Chemical constituents from lythrum salicaria L.; Journal of Chinese Pharmaceutical Sciences; 2015; 1190-1195; vol. 50(14).

HAIR COMPOSITION

The invention relates to an oral or topical composition which produces a benefit of hair fibre growth. In particular, the oral or topical composition comprises a nuclear factor erythroid-2 related factor 2 agonist and a liver X receptor agonist, wherein the amounts of each of the nuclear factor erythroid-2 related factor 2 agonist and the liver X receptor agonist produce a synergistic benefit of hair fibre growth.

Figure 1:
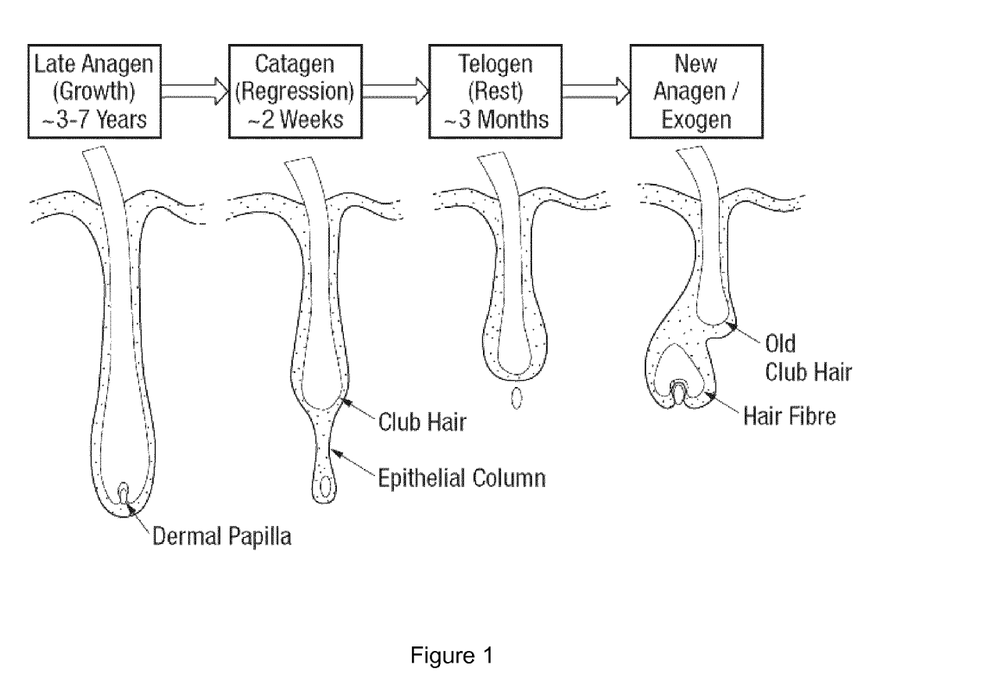
FIG. 1 which shows follicular cycling through phases of organ growth and hair fibre production (anagen), cessation of fibre growth and organ involution (catagen) and a quiescent phase (telogen)

The main function of the hair follicle is to produce a hair fibre. The hair follicle develops from the embryonic epidermis as an epidermal finger which differentiates into the fibre, the outer root sheath (ORS) and the inner root sheath (IRS). FIG. 1 illustrates how mature follicles undergo follicular cycling through phases of organ growth and hair fibre production (anagen) for 3-7 years, cessation of fibre growth and organ involution (catagen) over about 2 weeks and a quiescent phase (telogen) which lasts about 3 months where the organ rests and the hair fibre remains anchored but no longer grows before the hair fibre falls (exogen) and is regenerated to start the cycle again (Dry, J Genet 16, 281-340 (1926), Chase, Physiol Rev 34, 1, 113-26 (1954) and Kligman, J Invest Dermatol 33, 307-16 (1959)).

Moi et al (Proc. Natl. Acad. Sci. U.S.A., 91, 21, 9926-30 (October 1994)) discloses that nuclear factor erythoid-2 related factor 2 (known as NRF2) is a transcription factor (protein) that in humans is encoded by the NFE2L2 gene. According to Lee et al (J. of Biochem & Mol Biol. 37, 139-143 (2004)) and Hybertson et al (Mol Aspects Med. 32, 234-46 (2011)), NRF2 has been shown to be involved in the defence against oxidative injury in various tissues. Under basal conditions, NRF2 is inactive and bound in the cytoplasm by cytosolic regulatory protein Kelch-like ECH-associated protein 1 (Keap1). According to Itoh et al (Genes Dev., 13, 1, 76-86 (January 1999)) the protein Cullin 3 degrades NRF2 by ubiquitination. According to Kobayashi et al (Mol. Cell. Biol., 24, 16, 7130-9 (August 2004)) Keap1 helps Cullin 3 ubiquitinate NRF2. When NRF2 is ubiquitinated, it is transported to the proteasome where it is degraded and its components recycled such that under normal conditions, NRF2 has a half-life of only 20 minutes.

Yamamoto et al (Mol. Cell (Biol., 28, 8, 2758-70 (April 2008)) and Sekhar et al (Toxicol. Appl. Pharmacol., 244, 1, 21-6 (June 2009)) disclose that oxidative stress or electrophilic stress disrupts critical cysteine residues in Keap1, disrupting the Keap1-Cullin 3 ubiquitination system. When NRF2 is not ubiquitinated, it builds up in the cytoplasm and translocates into the nucleus. Itoh et al (Biochem. Biophys. Res. Commun., 236, 2, 313-22 (July 1997)) disclose that in the nucleus, NRF2 combines (forms a heterodimer) with a small Maf protein (a transcription factor) and binds to small regions of DNA known as Antioxidant Response Elements (ARE's) in the upstream promoter region of many antioxidative genes, and initiates their transcription. Thus induction of ARE is a marker of NRF2 up-regulation.

According to Lee et al and Hybertson et al, the antioxidant genes include "phase II" enzymes such as NADP(H): quinone oxidoreductase (NQO-1) and hemoxygenase-1 (HO-1). Increased oxidative stress has been shown to have a detrimental effect on hair pigmentation (Lu et al, J Invest Dermatol, 129, 1790-804 (2009); Arck et al, FASEB J. 2, 1567-9 (2006)). Therefore up-regulation of NQO-1 and HO-1 are also markers of NRF2 up-regulation.

Hair ageing is a major age-related consumer issue (hair loss, thinning hair, loss of shine, increased number of grey hairs, etc).

Biological routes for hair growth or preventing hair greying provide effective opportunities to target consumer hair issues. Currently, Minoxidil™ and Finasteride™ are the only clinically proven, mildly effective products available for hair growth and both are classified as medicines and therefore not suitable for cosmetic use. The identification of cosmetic ingredients which are able to boost hair growth, maintain anagen and/or prevent catagen may prove to be effective anti ageing treatments to prevent or attenuate some of the symptoms associated with hair ageing.

WO 2014/095289 (Unilever et al.) discloses that NRF2 agonists (determined by measuring NQO-1 and HO-1 protein up-regulation in hair follicle cells) were observed to promote hair fibre growth in a hair growth model. Example 5 disclosed that NQO-1 is detected in both the inner and outer hair follicle root sheath, and that treatment of hair follicles with sulforaphane, an NRF2 agonist, leads to up-regulation of HO-1 in the mesenchymal connective tissue sheath.

According to WO 2004/103320 (Unilever et al.), liver X receptor α/β (LXR α/β) are nuclear receptors known to be present in human keratinocytes where it plays an integral role in the regulation of cell proliferation and differentiation as well as lipid metabolism within the epidermis.

Database GNPD Mintel item XP002741680 ("Dr Dennis Gross Skincare: Nourishing Scalp Conditioner") discloses a hair care composition which contains several dozen ingredients. The "key ingredients" are identified as: adenosine, alpha lipoic acid, copper peptides, procyanidin B2, and retinol. Other ingredients include apple peel extract and β-sitosterol. Apple peel extract contains quercetin glycosides, but is essentially devoid of quercetin aglycone.

Database GNPD Mintel item XP002741681 ("Dr Dennis Gross: Anti-aging Scalp Serum") discloses a similar composition including the same "key ingredients" as XP002741680, but additionally Saw Palmetto is listed as a key ingredient.

Mundada & Shivhare ("Pharmacology of *Tridax procumbens* a Weed: Review", Intl. J. of Pharmtech Research 2, No. 2 p 1391-1394) review some of the pharmacological activities ascribed to *Tridax procumbens*. The leaves of the plant are said to "prevent falling of hair" and "promotes the growth of hair", Chemical analysis (described by Sawant & Godghate, "Preliminary phytochemical analysis of leaves of *Tridax procumbens* Linn.", Intl. J. of Science, Environment and Technology 2, no. 3 p 388-394) revealed that the leaves of the plant do not contain any phytosterols, such as brassicasterol etc.

Database GNPD Mintel item XP002741682 (Swanson Health Products: "All-in-one nutrient formula dietary supplement") discloses a ready-to-drink liquid composition "that has over 400 ingredients". Among the very large number of ingredients are lutein (at 1 mg per 30 ml, approx. 0.003 w/v %) and phytosterol complex (including β-sitosterol, stigmasterol and brassicasterol), at 25 mg per 30 ml (approx. 0.075 w/v %).

SUMMARY OF THE INVENTION

The inventors have observed synergistic induction of ARE (using a luciferase assay) in HaCaT immortalised human keratinocyte cells treated with a combination of 1 µM granilin, an NRF2 agonist, and 1 µM 22(R)-hydroxycholesterol, a liver X receptor α/β agonist. Synergy was also observed with combinations of 5 µM granilin and 1 µM 22(R)-hydroxycholesterol, 1 µM granilin and 10 µM 22(R)-hydroxycholesterol, and 5 µM granilin and 10 µM 22(R)- hydroxycholesterol. Synergies were also observed when using 3-[3-[[[2-chloro-3-(trifluoromethyl)phenyl]methyl](2,2-diphenylethyl)amino]propoxy]benzeneacetic acid hydrochloride (also known as GW 3965 hydrochloride and available from Tocris) and stigmasterol as the liver X receptor α/β agonists.

The inventors also observed up-regulation of hemoxygenase 1 protein in HaCaT immortalised human keratinocyte cells treated with a combination of 1 μM sulforaphane, an NRF2 agonist, and 10 μM 22(R)-hydroxycholesterol, a liver X receptor α/β agonist. Synergy was also observed with the combination of 0.05 μM sulforaphane and 10 μM 22(R)-hydroxycholesterol. Synergies were not seen with combinations of 0.01 μM sulforaphane and 10 μM 22(R)-hydroxycholesterol, 1 μM sulforaphane and 1 μM 22(R)-hydroxycholesterol, 0.05 μM sulforaphane and 1 μM 22(R)-hydroxycholesterol, and 0.01 μM sulforaphane and 1 μM 22(R)-hydroxycholesterol.

Also observed by the inventors was significant up-regulation of NQO-1 mRNA in human hair follicle cells treated with 10 μM sulforaphane and 5 μM 22(R)-hydroxycholesterol.

Thus in a first aspect of the invention, an oral or topical composition is provided, the oral or topical composition comprising a nuclear factor erythroid-2 related factor 2 agonist and a liver X receptor agonist, wherein the amounts of each of the nuclear factor erythroid-2 related factor 2 agonist and the liver X receptor agonist produce a synergistic benefit of hair fibre growth, wherein the oral or topical composition comprises ≤9, preferably ≤8% w/w β-sitosterol, wherein when the oral or topical composition comprises a catechin, the oral or topical composition comprises 0.001 to 90, preferably 0.005 to 70, most preferably 0.01 to 50% w/w catechins, wherein the oral or topical composition excludes pregnenolone, 4, 5-dihydrofuranodiene-6-one, epoxy santamarin, hydroquinone, longistyline, monacolin K, protoanemonin, N-(2,2,2-trifluoro-ethyl)-N-[4-(2,2,2-tri-fluoro-1-hydroxy-1-trifluoromethyl-ethyl)-phenyl]-benzenesulfonamide, dihydronepetalactone, iridomyrmecin, and dihydroactinidiolide, wherein when the oral or topical composition comprises guggelsterone and epigallocatechin gallate, the oral or topical composition excludes a guggelsterone to epigallocatechin gallate weight ratio of 1 to 28, and wherein when the oral or topical composition comprises sodium dilauramide glutamide lysine, the oral or topical composition excludes 0.3% w/w sodium dilauramide glutamide lysine.

In a second aspect of the invention, an oral or topical composition is provided, the oral or topical composition comprising a nuclear factor erythroid-2 related factor 2 agonist and a liver X receptor agonist, wherein the amounts of each of the nuclear factor erythroid-2 related factor 2 agonist and the liver X receptor agonist produce a synergistic induction of the antioxidant response element and/or up-regulation of hemoxygenase 1 in HaCaT immortalised human keratinocyte cells and/or up-regulation of NAD(P)H dehydrogenase (quinone) 1 in human hair follicle cells, wherein the oral or topical composition comprises ≤9, preferably ≤8% w/w β-sitosterol, wherein when the oral or topical composition comprises a catechin, the oral or topical composition comprises 0.001 to 90, preferably 0.005 to 70, most preferably 0.01 to 50% w/w catechins, wherein the oral or topical composition excludes pregnenolone, 4, 5-dihydrofuranodiene-6-one, epoxy santamarin, hydroquinone, longistyline, monacolin K, protoanemonin, N-(2,2,2-trifluoro-ethyl)-N-[4-(2,2,2-tri-fluoro-1-hydroxy-1-trifluoromethyl-ethyl)-phenyl]-benzenesulfonamide, dihydronepetalactone, iridomyrmecin, and dihydroactinidiolide, wherein when the oral or topical composition comprises guggelsterone and epigallocatechin gallate, the oral or topical composition excludes a guggelsterone to epigallocatechin gallate weight ratio of 1 to 28, and wherein when the oral or topical composition comprises sodium dilauramide glutamide lysine, the oral or topical composition excludes 0.3% w/w sodium dilauramide glutamide lysine.

Preferably, in the composition of the invention, the concentration of nuclear factor erythroid-2 related factor 2 agonist in the composition is at least 0.09 w/w % or 0.09 w/v %, preferably in the range 0.1-49 w/w % or 0.1-49 w/v %, more preferably in the range 0.2-25 w/w % or w/v %; and wherein the concentration of the liver X receptor agonist in the composition is at least 0.09 w/w % or 0.09 w/v %, preferably in the range 0.1-49 w/w % or 0.1-49 w/v %, more preferably in the range 0.2-25 w/w % or w/v %.

In a third aspect, the invention provides an oral or topical composition comprising a nuclear factor erythroid-2 related factor 2 agonist and a liver X receptor agonist, wherein the oral or topical composition comprises ≤9, preferably ≤8% w/w β-sitosterol, wherein when the oral or topical composition comprises a catechin, the oral or topical composition comprises 0.001 to 90, preferably 0.005 to 70, most preferably 0.01 to 50% w/w catechins;

wherein the oral or topical composition excludes pregnenolone, 4, 5-dihydrofuranodiene-6-one, epoxy santamarin, hydroquinone, longistyline, monacolin K, protoanemonin, N-(2,2,2-trifluoro-ethyl)-N-[4-(2,2,2-tri-fluoro-1-hydroxy-1-trifluoromethyl-ethyl)-phenyl]-benzenesufonamide, dihydronepetalactone, iridomyrmecin, and dihydroactinidiolide;

and wherein when the oral or topical composition comprises guggelsterone and epigallocatechin gallate, the oral or topical composition excludes a guggelsterone to epigallocatechin gallate weight ratio of 1 to 28; and wherein when the oral or topical composition comprises sodium dilauramide glutamide lysine, the oral or topical composition excludes 0.3% w/w sodium dilauramide glutamide lysine; wherein the concentration of nuclear factor erythroid-2 related factor 2 agonist in the composition is at least 0.09 w/w % or 0.09 w/v %, preferably in the range 0.1-49 w/w % or 0.1-49 w/v %, more preferably in the range 0.2-25 w/w % or w/v %; and wherein the concentration of the liver X receptor agonist in the composition is at least 0.09 w/w % or 0.09 w/v %, preferably in the range 0.1-49 w/w % or 0.1-49 w/v %, more preferably in the range 0.2-25 w/w % or w/v %.

In a fourth aspect, the invention provides an oral or topical composition comprising a nuclear factor erythroid-2 related factor 2 agonist and a liver X receptor agonist which agonists, in combination in the composition, exert a synergistic effect on the induction of the antioxidant response element ("ARE"), wherein the oral or topical composition comprises ≤9, preferably ≤8% w/w β-sitosterol, wherein when the oral or topical composition comprises a catechin, the oral or topical composition comprises 0.001 to 90, preferably 0.005 to 70, most preferably 0.01 to 50% w/w catechins;

wherein the oral or topical composition excludes pregnenolone, 4, 5-dihydrofuranodiene-6-one, epoxy santamarin, hydroquinone, longistyline, monacolin K, protoanemonin, N-(2,2,2-trifluoro-ethyl)-N-[4-(2,2,2-tri-fluoro-1-hydroxy-1-trifluoromethyl-ethyl)-phenyl]-benzenesulfonamide, dihydronepetalactone, iridomyrmecin, and dihydroactinidiolide;

and wherein when the oral or topical composition comprises guggelsterone and epigallocatechin gallate, the oral or topical composition excludes a guggelsterone to epigallocatechin gallate weight ratio of 1 to 28; and wherein when the oral or topical composition comprises sodium dilauramide glutamide lysine, the oral or topical composition excludes 0.3% w/w sodium dilauramide glutamide lysine;

wherein the concentration of nuclear factor erythroid-2 related factor 2 agonist in the composition is at least 0.09 w/w % or 0.09 w/v %, preferably in the range 0.1-49 w/w % or 0.1-49 w/v %, more preferably in the range 0.2-25 w/w % or w/v %; and wherein the concentration of the liver X receptor agonist in the composition is at least 0.09 w/w % or 0.09 w/v %, preferably in the range 0.1-49 w/w % or 0.1-49 w/v %, more preferably in the range 0.2-25 w/w % or w/v %.

In a fifth aspect of the invention, an oral or topical anti-ageing composition according to any of the first to fourth aspects of the invention for use in promoting hair fibre growth is provided.

In a sixth aspect the invention provides for the use of a nuclear factor erythroid-2 related factor agonist and a liver X receptor agonist as active agents in an oral or topical composition for benefiting hair fibre growth and/or inducing the Antioxidant Response Element (ARE). The use may be for purely cosmetic and non-medical purposes.

Preferably the nuclear factor erythroid-2 related factor agonist is used in the composition at a concentration above 0.09 w/w % or 0.09 w/v %, more preferably at a concentration in the range 0.1-49 w/w % or w/v %, and typically at a concentration in the range 0.2-25 w/w % or w/v %. The liver X receptor agonist is similarly preferably used in the composition at a concentration above 0.09 w/w % or 0.09 w/v %, more preferably at a concentration in the range 0.1-49 w/w % or w/v %, and typically at a concentration in the range 0.2-25 w/w % or w/v %. It will be apparent to those skilled in the art that the composition may be solid or liquid.

Examples of preferred nuclear factor erythroid-2 related factor agonists and liver X receptor agonists are detailed elsewhere in the present specification, as are detailed elsewhere in the present specification, as are other optional components of the composition. The nuclear factor erythroid-2 related factor agonist and liver X receptor agonist may be the sole active agents in the composition.

BRIEF DESCRIPTION OF THE FIGURES

The invention is exemplified with reference to.

DETAILED DESCRIPTION OF THE INVENTION

The nuclear factor erythoid-2 related factor 2 agonist may be selected from the group consisting of allyl isothiocyanate, andrographolide, apigenin, Asiatic acid, baicalein, tert-butyl hydroxyquinone, (+)-catechin, chrysin, chrysin dimethylether, curcumin, docosahexaenoic acid, epigallocatechin gallate, esculetin, fraxetin, galangin, genistein, granilin, guaiacol, hesperetin, 4-hydroxy-3-methoxyacetophenone, jasmonic acid, kaempferol, (S)-(+)-ketoprofen, kinetin, kinetin riboside, gamma linolenic acid, lipoic acid, lutein, luteolin, lycopene, nordihydroguaiaretic acid, parthenolide, peonidin chloride, phloroglucinol carboxaldehyde, pinocembrin, pinostrobin, protocatechinic acid, pterostilbene, quercetin, rauwolscine, resveratrol, silibinin, silichristin, sulforaphane, taxifolin, theaflavin, vanillyl acetone, trans-zeatin riboside, chamomile oil, parsley peel ethanol extract, sage peel ethanol extract, sour orange peel ethanol extract, tangerine peel ethanol extract and thyme peel ethanol extract. Preferably the nuclear factor erythroid-2 related factor 2 agonist is selected from the group consisting of allyl isothiocyanate, apigenin, Asiatic acid, catechin, curcumin, docosahexaenoic acid, epigallocatechin gallate, esculetin, genistein, hesperetin, kaempferol, lipoic acid, lutein, luteolin, lycopene, pinocembrin, pinostrobin, quercetin, resveratrol, sulforaphane, theaflavin, vanillyl acetone, chamomile oil, sour orange peel ethanol extract and tangerine peel ethanol extract.

Preferably in a composition in accordance with any of the aforementioned aspects, the nuclear factor erythroid-2 related factor 2 agonist comprises a eudesmane sesquiterpenoid and/or a ring A-hydroxylated isoalantolactone. Examples of eudesmane sesquiterpenoids include, in particular:

α-eudesmol, β-eudesmol, γ-eudesmol, (+)-4-epi-cryptomeridiol, (1R,2R,4aS,5R,8aR)-2-isopropyl-4a-methyl-8-methylenedecahydronaphthalene-1,5-diol, 1β-hydroxy-6,7α-dihydroxyeudesm-4(15)-ene, 10-epi-γ-eudesmol, 1beta,6alpha-dihydroxy-4(14)-eudesmene, 4(15)-eudesmene-1beta,7alpha-diol, 4,6-Diene-1beta,14-dihydroxyeudesma-3-one, alpha-Cyperone (CHEBI:80919) corymbolone (CHEBI:65659), cryptomeridiol (CHEBI:67796), Cycloeudesmol CHEBI:4001), Cyperol (CHEBI:80813) cyperusol C (CHEBI:69847) dihydroagarofuran, Encelin (CHEBI:4790) Eudesobovatol A Farinosin (CHEBI:4977) Granilin (CHEBI:5536) isoalantolactone (CHEBI:5981), Isocyperol (CHEBI:80836), Ivalin (CHEBI:6077), Kikkanol A (CHEBI:81209), Kikkanol B (CHEBI:81210), Kikkanol C (CHEBI:81211), and Samboginone (CHEBI:67795)

A preferred example is granilin.

The liver X receptor agonist may be selected from the group consisting of a compound of general formulae:

wherein;
R represents a hydrogen, a hydroxyl, a keto, an acetyl, a $C_1$ to $C_7$, substituted or unsubstituted, branched or unbranched, saturated or unsaturated alkyl group, or a substituted or unsubstituted, branched or unbranched, unsaturated $C_8$ alkyl group;
$R_1$ represents a lower alkyl group, a hydrogen or $COR_6$;
$R_2$ represents a hydrogen, a halogen or hydroxyl group;
$R_3$ represents a hydrogen, a hydroxyl, a halogen, a keto or lower alkyl group;
$R_4$ represents a hydrogen, a hydroxyl, or a keto group;
$R_5$ represents a hydrogen, a hydroxyl, a halogen or lower alkyl group;
$R_6$ represents a lower alkyl group;
X represents a hydrogen, a methyl or a halogen;
Y represents a hydrogen, a hydroxyl, a acetyl or a keto group;
a plant extract, 3-[3-[[[2-chloro-3-(trifluoromethyl)phenyl]methyl](2,2-diphenylethyl)amino]propoxy]benzeneacetic acid hydrochloride, β-sitosterol, and mixtures thereof,
wherein the plant extract is selected from the group consisting of an acetone extract of Dragon's blood resin (*Daemorgos draco*), an ethyl acetate extract of Damar gum, a non-saponified methanol extract of Nettle (*Lamium albim*), a methanol extract of Breuzihno resin, a hexane extract of red seaweed, a methanol extract of mastic gum (*Pistacia lentiscus*), a dichloromethane extract of mountain ash berry, a dichloromethane extract of plantain leaves, and mixtures thereof.

A "lower alkyl" as employed herein includes both straight and branched chain radicals of up to four carbon atoms, examples of suitable groups are outlined above.

Preferably R represents a hydrogen, a hydroxyl, a keto or a $C_1$ to $C_4$ substituted or unsubstituted alkyl group, most preferably R represents a substituted unbranched $C_1$ to $C_4$ alkyl group. Alternatively R represents —H, —OH, =O, —COCH$_3$, =COHCH$_3$, =CHCH$_3$, =CHCH$_2$OH, and —OCOCH$_3$, in particular R represents —C(CH$_3$)(CH$_2$)$_3$C(CH$_3$)$_2$.

Preferably when the liver X receptor agonist is according to general formula A, then Y is a keto group. Preferably when the liver X receptor agonist is according to general formula B, then $R_1$ represents a hydrogen and Y represents a hydroxyl group, a hydrogen or an acetyl group.

The bond by which the R group is linked to the carbon at position 17 will depend on the nature of the R group (indicated by wavy bond). When R is an alkyl group, this group may be linked to the carbon at position 17 via a saturated or unsaturated bond, preferably an unsaturated bond.

For the purpose of the present invention, R may represent a hydroxyl, a keto or an acetyl group. R may also represent a $C_1$ to $C_7$ (i.e. including $C_1$, $C_2$, $C_3$, $C_4$, $C_5$, $C_6$ and $C_7$) substituted or unsubstituted, saturated or unsaturated, branched or unbranched alkyl group. Preferably said $C_1$ to $C_7$ alkyl group comprises at least one substituted group selected from hydroxyl, keto and acetyl groups and R may in particular represent substituted alkyl groups having two and three of said substitutions. More preferably the alkyl groups have undergone substitution with one or more keto or hydroxyl groups. Further preferred is an alkyl R group substituted at one or more positions corresponding or equivalent to $C_{20}$, $C_{21}$, $C_{22}$ and $C_{23}$ shown in the figure below:

Where the substitution is with a keto group, this is most preferably bonded to $C_{20}$, whereas when substitution is with a hydroxyl group, this is most preferably bonded to a carbon at $C_{21}$ and/or $C_{22}$.

It is preferred that the alkyl R group remains unbranched as this helps to maintain a favoured linear configuration, however in the event that the alkyl group is branched, said branches preferably comprise 2 carbons, more preferably 1 carbon.

Where the R group is an alkyl group as described above, this will preferably have some degree of unsaturation. Preferably unsaturation occurs in the form of one or more substituted keto groups.

Where R represents an unsaturated $C_1$ to $C_8$ alkyl group, it is most preferred that this group has the formula —C(CH$_3$)(CH$_2$)$_3$C(CH$_3$)$_2$.

While not wishing to be bound by any theory, it is believed that it is the conformation of the R group of a molecule according to the general formulae provided herein which determines the correct interaction with the active site and thereby the activation of liver X receptor alpha. More particularly from computer modelling of molecular structures, it is believed, where the R group is a carbon chain, that in order to allow correct active site interaction, the R group should preferably adopt a substantially linear conformation. This may be achieved in those molecules wherein the R group is a substantially linear carbon chain and/or has at least one unsaturated C—C bond.

It is also believed that the more effective agonists of liver X receptor alpha comprise a small R group. In a preferred embodiment, the R group of the liver X receptor alpha agonist therefore represents a hydrogen, a hydroxyl, a keto or an unsubstituted or, more preferably, substituted $C_1$ to $C_4$ alkyl group. Preferably substitution occurs at $C_{20}$ or $C_{21}$ within the alkyl group. Where the R group is an alkyl group, it is preferred that this forms an unsaturated bond with $C_{17}$ of the ring structure.

In a preferred embodiment, R represents a hydrogen, a hydroxyl, a keto or a substituted/unsubstituted $C_1$ to $C_4$ alkyl group. Suitable unsubstituted groups include methyl, ethyl, n-propyl, isopropyl, n-butyl, isobutyl or tert-butyl.

In a preferred embodiment $R_1$ is a hydrogen. $R_2$ represents a hydrogen, a halogen, preferably chlorine, or a hydroxyl group. Preferably $R_2$ represents a hydrogen. $R_3$ represents a hydrogen, a halogen, preferably a fluorine or chlorine, a keto or a lower alkyl group. Preferably $R_3$ is either a keto group or a hydrogen. In a most preferred embodiment $R_3$ is a hydrogen. Preferably $R_4$ and $R_5$ represent a hydroxyl group or hydrogen. Most preferably these represent a hydrogen. $R_6$ represents a lower alkyl, preferably a methyl group. X preferably represents a hydrogen, a fluorine or a chlorine, most preferably X is a hydrogen. Preferably Y represents a hydrogen, a hydroxyl or a keto group. When Y is a hydrogen, in a compound according to general formula A, a double bond may form between $C_{16}$ and $C_{17}$. In a compound according to formula B, when Y is hydrogen, $R_1$ is preferably a hydrogen or —$COR_6$. Preferably when Y is a keto group, the liver X receptor agonist conforms to general formula A, whereas when Y is a hydroxyl group, the liver X receptor agonist preferably conforms to general formula B. In a most preferred embodiment the liver X receptor agonist conforms to formula A wherein Y is a keto group.

When R is a hydrogen or a hydroxyl group, Y is preferably a keto group in an liver X receptor agonist according to formula A. When R is —$COCH_3$, Y is preferably a hydrogen or a keto group in a liver X receptor agonist according to either formulae A or B, preferably according to formula A. When R is =$CHCH_3$ or —$OCOCH_3$, Y is most preferably a keto group in a liver X receptor agonist according to general formula A. When R is =$CHCH_2OH$, Y is preferably either:

(a) a hydrogen in a liver X receptor agonist according to general formula A, wherein $R_4$ is preferably a hydroxyl group; or
(b) a hydroxyl group in a liver X receptor agonist according to formula B wherein $R_1$ is a hydrogen.

When R is —$C(CH_3)(CH_2)_3C(CH_3)_2$, Y is preferably a hydrogen in a liver X receptor agonist according to formula B wherein $R_1$ is also a hydrogen.

Preferably the liver X receptor agonist is selected from the group consisting of 4-androsten-3,16-dione, androst-4-ene-3,6,16-trione, 4-androsten-17β-ol-3,16-dione acetate, 16-ketotestosterone, 3β-acetoxypregna-5,16-dien-20-one, 3β-acetoxypregna-5-en-20-one, 3β-hydroxypregna-5,16-dien-20-one, 3β-hydroxypregn-5-en-20-one, 5,16-dien-pregnane-3,20-diol, 4,16-dienpregna-3,20-dione, 4,17(20)-(trans)-pregnadien-3,16-dione, 4-pregnen-3,16,20-trione, 4,17(20)-pregnadien-11β,21-diol-3-one, 5,17(20)-pregnadien-3,16-diol, 5-pregnen-3β,16α,21-triol-20-one, 24-hydroxychol-4-en-3-one, cholesta-5,24-dien-3β-ol, (3β)-3-hydroxyurs-12-en-28oic acid, cis-guggulsterone, desmosterol, 22(R)-hydroxycholesterol, stigmasterol, brassicasterol, 7-hydroxycholesterol, and mixtures thereof. More preferably the liver X receptor agonist is selected from the group consisting of desmosterol, stigmasterol, brassicasterol, β-sitosterol, and mixtures thereof, or is selected from the group consisting of 22(R)-hydroxycholesterol, stigmasterol, and 3-[3-[[[2-chloro-3-(trifluoromethyl)phenyl]methyl](2,2-diphenylethyl)amino]propoxy]benzeneacetic acid (referred to herein as GW 3965) and/or salts thereof (especially the hydrochloride salt), and mixtures of the aforementioned compounds.

The topical composition of the first to fourth aspects of the invention will comprise a dermatologically acceptable vehicle which acts as a diluent, a dispersant and/or a carrier not only for the ingredients which are essential for the invention but also for any other optional but often preferred ingredients. The dermatologically acceptable vehicle may be water or oil-based, anhydrous or an emulsion, with water-in-oil or oil-in-water emulsions being generally preferred. If water-based or an emulsion, the dermatologically acceptable vehicle comprises 5 to 99, most preferably 40 to 80% w/w of the topical composition, including all ranges subsumed therein.

The dermatologically acceptable vehicle may also comprise organic solvents, such as alkanols and ester oils. Typical examples of alkanols are ethyl alcohol and isopropyl alcohol. Typical examples of ester oils are isopropyl myristate, cetyl myristate, 2-octyldodecyl myristate, avocado oil, almond oil, olive oil, and neopentylglycol dicaprate.

The dermatologically acceptable vehicle may also comprise 0.1 to 50% w/w emollients such as alcohols (for example cetyl alcohol), silicone oils and esters, and esters. Silicone oils include cyclic or linear polydimethylsiloxanes containing from 3 to 9, preferably from 4 to 5, silicon atoms. Non-volatile silicone oils include polyalkyl siloxanes (for example polydimethylsiloxanes), polyalkylaryl siloxanes and polyether siloxane copolymers. Esters include alkenyl or alkyl esters of fatty acids having 10 to 20 carbon atoms (for example isoarachidyl neopentanoate, isononyl isononanoate, oleyl myristate, oleyl stearate and oleyl oleate), ether-esters (for example fatty acid esters of ethoxylated fatty alcohols), polyhydric alcohol esters (for example ethylene glycol mono- and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters), wax esters (for example beeswax, spermaceti, stearyl stearate and arachidyl behenate), and sterols esters (for example cholesterol fatty acid esters).

The dermatologically acceptable vehicle may also comprise fatty acids having from 10 to 30 carbon atoms (for example pelargonic, lauric, myristic, palmitic, stearic, isostearic, oleic, linoleic, arachidic, behenic and erucic acids).

The dermatologically acceptable vehicle may also comprise 0.2 to 25, preferably 0.5 to 15% w/w humectant which increase the effectiveness of the emollient, reduces scaling, stimulates removal of built-up scale and improves skin feel. Typically the humectants is a polyhydric alcohol (for example glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof). Preferably the humectant is glycerol.

The dermatologically acceptable vehicle may also comprise 0.0001 to 5%, preferably 0.001 to 1%, most preferably 0.01 to 0.5% w/w thickener (for example cross-linked acrylates such as Carbopol 982, hydrophobically-modified acrylates such as Carbopol 1382, cellulosic derivatives (such as sodium carboxymethylcellulose, hydroxypropyl methylcellulose, hydroxypropyl cellulose, hydroxyethyl cellulose, ethyl cellulose and hydroxymethyl cellulose) and natural gums (such as guar, xanthan, sclerotium, carrageenan, and pectin)).

The topical composition of the first and second aspects of the invention may also comprise 0.001 to 40, preferably 0.001 to 20, most preferably 0.01 to 5% w/w surfactant selected from the group consisting of anionic, nonionic, cationic, amphoteric surfactants, and mixtures thereof. Preferred nonionic surfactants include a C10-C20 fatty alcohol or acid hydrophobe condensed with from 2 to 100 moles of ethylene oxide or propylene oxide per mole of hydrophobe, mono- and di-fatty acid esters of ethylene glycol, fatty acid monoglyceride, sorbitan-, mono- and di-C8-C20 fatty acids, block copolymers (such as ethylene oxide/propylene oxide), polyoxyethylene sorbitan, and alkyl polyglycosides and saccharide fatty amides (such as methyl gluconamides).

Preferred anionic surfactants include soap, alkyl ether sulfate and sulfonates, alkyl sulfates and sulfonates, alkylbenzene sulfonates, alkyl and dialkyl sulfosuccinates, C8-C20 acyl isethionates, acyl glutamates, and C8-C20 alkyl ether phosphates.

The topical composition of the first and second aspects of the invention may also comprise other optional ingredients such as fragrances, fillers (such as talc and silica), alpha-hydroxy acids, beta-hydroxy acids (such as salicylic acid), zinc salts (such as zinc pyrithione), preservatives, sunscreens, both organic and inorganic (such as derivatives of para-aminobenzoic acid (PABA), cinnamate and salicylate (for example avobenzophenone, octyl methoxycinnamate and 2-hydroxy-4-methoxy benzophenone, zinc oxide and titanium dioxide), and anti-dandruff actives (such as ketoconazole, climbazole, and zinc pyrithione).

The topical composition of the first and second aspects of the invention may also comprise 0.01 to 10, more preferably 0.1 to 5, most preferably 0.5 to 3% w/w conditioning silicone (such as dimethiconol, silicone gums and amino functional silicones). In combination with conditioning silicone, the topical composition of the invention will normally comprise 0.01 to 5, preferably 0.05 to 1, more preferably 0.08 to 0.5% w/w cationic polymer for enhancing deposition of the silicone on hair fibres (such as dimethyldiallylammonium chloride homopolymer (Polyquaternium 6), copolymers of acrylamide and dimethyldiallylammonium chloride (Polyquaternium 7), mineral acid salts of amino-alkyl esters of homo- and co-polymers of unsaturated carboxylic acids having from 3 to 5 carbon atoms (as described in U.S. Pat. No. 4,009,256), cationic polyacrylamides (as described in WO 95/22311), and cationic polysaccharide polymers (for example polymeric quaternary ammonium salts of hydroxyethyl cellulose reacted with lauryl dimethyl ammonium-substituted epoxide (Polyquaternium 24), and guar hydroxypropyltrimethylammonium chloride)).

The topical composition of the first and second aspects of the invention can be manufactured by mixing the ingredients in no particular order and usually at 70 to 80° C. and under atmospheric pressure. The packaging for the topical composition of the invention can be a patch, bottle, tube, roll-ball applicator, propellant driven aerosol device, squeeze container or lidded jar.

The invention also provides a method for promoting hair fibre growth comprising the step of applying to hair fibres and/or scalp the topical composition of the first or second aspects of the invention.

The oral composition of the first and second aspects of the invention may be in the form of a solid, a slurry, a solution, a suspension, a gel or an emulsion. When solid, the oral anti-ageing composition of the first aspect of the invention may be in the form of a supplement of one or more unit dosages such as capsules, cachets, lozenges, pills, tablets, caplets, each comprising a predetermined amount of the essential ingredients of the invention.

More specifically, the oral composition of the first and second aspects of the invention may be selected from the group of foodstuffs consisting of a beverage (for example a fruit or tea (for example *Camellia sinensis*) based beverage, a supplement, a soup (in dry, paste or liquid form), margarine, a ready-to-eat meal, a dressing, a mayonnaise, mustard, a tomato-based condiment, a sauce, a seasoning (for example as unit doses in the form of a powder, a compressed powder in the form of, for example, a cube, a liquid or suspension, or a gel), a yoghurt and a frozen confection. By "frozen confection" is meant a sweet-tasting fabricated foodstuff intended for consumption in the frozen state (i.e. under conditions wherein the temperature of the foodstuff is less than 0° C., and preferably under conditions wherein the foodstuff comprises significant amounts of ice). Frozen confections include ice cream, sorbet, sherbet, frozen yoghurt, water ice, milk ice and the like. Preferably the frozen confection has a total solids content (i.e. the sum of the weights of all the ingredients other than water, expressed as a percentage of the total weight) of at least 20%, more preferably at least 25%. Frozen confections may be aerated or unaerated. Preferably the frozen confection is aerated. The frozen confection may be manufactured by any suitable process, typically by preparing a mix of ingredients; then pasteurising and optionally homogenising the mix; and then freezing and optionally aerating the mix to produce the frozen confection.

The invention also provides a method for promoting hair fibre growth comprising the step of imbibing the oral composition of the first or second aspects of the invention.

Example 1

HaCaT Cell with Antioxidant Response Element (ARE) Reporter Gene Assay

HaCaT (immortal human keratinocyte) cells (P42) were stored in liquid nitrogen and revived in DMEM containing 10% FBS. The cells were sub-cultured and cryostocks made in 10% DMEM containing 10% DMSO from the first two passages.

To generate a stable cell line, the optimal antibiotic concentration was determined for selecting stable cell colonies. A kill curve was performed using untransfected HaCaT cells to evaluate their hygromycin B sensitivity (as the ARE-luciferase construct to be used for transfection contains the gene for hygromycin B resistance). HaCaT cells were plated in a 24-well tissue culture plate at a cell density of ~80,000 cells per well. 24 hours later the cells were treated with different concentrations of Hygromycin B (ranging from 100 µg/ml to 800 µg/ml for seven days).

pGL4.37 (luc2P/ARE/Hygro) vector (Promega Cat. No. #E3641) transformed into DH5α competent cells (Invitrogen Cat. No. #18263-012). These were then plated on to an LB-ampicillin plate and kept overnight at 37° C. in an incubator.

The next day, single colonies were picked and inoculated in 5 ml LB Amp medium and kept at 37° C. for 8 hours in a shaker incubator at 250 rpm. The starter culture was then inoculated at 1:100 in 100 ml LB Amp medium. 24 hours later, the culture was harvested and transfection grade plasmid prepared using Sigma's Plasmid Midiprep Kit (Cat. No. #PLD35-1KT).

HaCaT cells were plated in 6-well tissue culture plate at a cell density of 500,000 cells per well. After 24 hours, the cells were transfected with 2 µg of endotoxin-free transfection grade pGL4.37 [luc2P/ARE/Hygro] vector in duplicates using Lipofectamine 2000 Reagent (Invitrogen) as per manufacturer's protocol. After transfection, HaCaT cells were allowed to grow and to express the protein for Hygromycin B resistance under non-selective conditions for 24 hours. One day post transfection cells were treated with Hygromycin B at a concentration of 400 µg/ml to initiate the antibiotic selection pressure. For the selection of stably expressing cells, HaCaT cells were grown in 10% DMEM medium containing 400 µg/ml of Hygromycin B. Under Hygromycin B selective conditions, resistant cells will outgrow non-resistant cells thereby resulting in a polyclonal population of stably-expressing cells. Stably expressing HaCaT cells were fed every 2-3 days with 400 µg/ml Hygromycin B selection medium. After 3 weeks of selection with 400 µg/ml of Hygromycin B medium stable pools were observed on the plate. Individual clones were picked using cloning rings and transferred to 96-well plate and expanded up to T25 $cm^2$ flask. Out of a dozen individual clones, clone 7 was chosen and validated for expression of luciferase upon treatment with D,L-sulforaphane.

HaCaT_ARE_luc2P_Clone_7 cells were seeded in a 96 well plate at a cell density of ~7.5×10³ cells per well. 24 hours later D, L-sulforaphane was added at increasing concentrations (0 µM, 0.2 µM, 0.4 µM, 0.6 µM, 0.8 µM and 1 µM). A standard curve for the luciferase assay was generated for relative light units (RLU) for HaCaT_ARE_Clone_7 cells treated with increasing concentrations of D,L-sulforaphane.

HaCaT_ARE_luc2P_Clone_7 cells were seeded in 96 well plates at a cell density of ~7,500 cells per well. All test compounds were added to the cells at a final dilution of 1:1000 and the luciferase assay performed.

The following combinations of test compounds were evaluated in the assay:

(a) granilin, an NRF2 agonist, and 22(R)-hydroxycholesterol, a liver X receptor α/β agonist;

(b) granilin and 3-[3-[[[2-chloro-3-(trifluoromethyl)phenyl]methyl](2,2-diphenylethyl) amino]propoxy]benzeneacetic acid hydrochloride (also known as GW 3965 hydrochloride and available from Tocris), a liver X receptor α/β agonist; and (c) granilin and stigmasterol, a liver X receptor α/β agonist.

Results

The results are summarised in Table 1 from which it is apparent that synergistic induction of ARE (using a luciferase assay) in HaCaT immortalised human keratinocyte cells treated with a combination of 1 µM granilin, an NRF2 agonist, and 1 µM 22(R)-hydroxycholesterol, a liver X receptor α/β agonist was observed. Synergy was also observed with combinations of 5 µM granilin and 1 µM 22(R)-hydroxycholesterol, 1 µM granilin and 10 µM 22(R)-hydroxycholesterol, and 5 µM granilin and 10 µM 22(R)-hydroxycholesterol. Synergies were also observed when using 3-[3-[[[2-chloro-3-(trifluoromethyl)phenyl]methyl](2,2-diphenylethyl)amino]propoxy]benzeneacetic acid hydrochloride (also known as GW 3965 hydrochloride and available from Tocris) and stigmasterol as the liver X receptor α/β agonists.

TABLE 1

Results of treatment of HaCaT cell with antioxidant response element (ARE) reporter gene with granilin (NRF2 agonist) and the liver X receptor α/β agonists 22(R)-hydroxycholesterol, GW 3965 hydrochloride and stigmasterol (n = 3).

| Test compounds | RLU |
| --- | --- |
| 1 µM granilin | 3.77 ± 0.31 |
| 5 µM granilin | 15.04 ± 0.18 |
| 1 µM 22(R)-hydroxycholesterol | 1.17 ± 0.03 |
| 10 µM 22(R)-hydroxycholesterol | 0.67 ± 0.01 |
| 1 µM granilin + 1 µM 22(R)-hydroxycholesterol | 6.77 ± 0.08 |
| 5 µM granilin + 1 µM 22(R)-hydroxycholesterol | 75.00 ± 2.18 |
| 1 µM granilin + 10 µM 22(R)-hydroxycholesterol | 4.94 ± 0.06 |
| 5 µM granilin + 10 µM 22(R)-hydroxycholesterol | 17.91 ± 0.08 |
| 1 µM granilin | 3.77 ± 0.31 |
| 5 µM granilin | 15.04 ± 0.18 |
| 1 µM GW 3965 hydrochloride | 1.02 ± 0.02 |
| 10 µM GW 3965 hydrochloride | 0.63 ± 0.01 |
| 1 µM granilin + 1 µM GW 3965 hydrochloride | 7.98 ± 0.33 |
| 5 µM granilin + 1 µM GW 3965 hydrochloride | 44.30 ± 0.14 |
| 1 µM granilin + 10 µM GW 3965 hydrochloride | 7.21 ± 0.49 |
| 5 µM granilin + 10 µM GW 3965 hydrochloride | 46.01 ± 1.23 |
| 1 µM granilin | 3.77 ± 0.31 |
| 5 µM granilin | 15.04 ± 0.18 |
| 1 µM stigmasterol | 0.78 ± 0.02 |
| 10 µM stigmasterol | 0.69 ± 0.00 |
| 1 µM granilin + 1 µM stigmasterol | 11.02 ± 0.04 |
| 5 µM granilin + 1 µM stigmasterol | 100.93 ± 5.39 |
| 1 µM granilin + 10 µM stigmasterol | 8.25 ± 0.01 |
| 5 µM granilin + 10 µM stigmasterol | 81.83 ± 2.31 |

Conclusions

Granilin, an NRF2 agonist appears to synergistically up-regulate induction of ARE in HaCaT immortalised human keratinocyte cells in combination with the liver X receptor α/β agonists 22(R)-hydroxycholesterol, GW 3965 hydrochloride and stigmasterol.

Example 2

HaCaT Cell with Antioxidant Response Element (ARE) Reporter Gene Assay

HaCaT (immortal human keratinocyte) cells (P42) were stored in liquid nitrogen and revived in DMEM containing 10% FBS. The cells were sub-cultured and cryostocks made in 10% DMEM containing 10% DMSO from the first two passages. Cells were routinely plated out in 6-well tissue culture dishes, at a seeding density of ~5000 cells/cm2 in 2 ml complete medium/well for 24 hours, and incubated at 37° C. in 5% CO2.

Test solutions were prepared in ethanol or DMSO and added directly to the cells and treated for 24 hours. The test solutions were prepared with selected concentrations of test material as set forth in Table 2. The cells were then pelleted.

All cell pellets were lysed on ice for 30 minutes in 1 ml cell lysis buffer per 2.5×106 cells. The lysis buffer contained 1% NP-40, 0.1% sodium deoxycholate, 0.1% SDS, 6 mM sodium chloride and 0.05 M Tris at pH 7.6. Protease inhibitor cocktail (1000×; Sigma P8340) was added prior to use at a level of 10 µl per ml of lysis buffer. The clarified cell lysate was frozen at −80° C. until needed.

The total protein concentration of each cell lysate was measured using the Pierce BCA protein assay kit. A set of eight standard solutions ranging from 0 to 1200 µg/ml protein was prepared from the supplied 2 mg/ml BSA stock solution. 10 µl of standard or cell lysate was added to duplicate wells of a flat-bottomed, 96-well microtitre plate. The reagent solution was prepared according to the kit instructions from 50 parts reagent A and 1 part reagent B. 200 µl of the final reagent was added to each well of the microtitre plate. The plate was mixed, covered and incubated at 37° C. for 30 minutes and absorbance read at 562 nm. A protein standard curve was constructed and used to determine the protein concentration of each cell lysate.

HO-1 ELISA (R & D Systems)

The hemeoxygenase-1 (HO-1) protein concentration of each cell lysate was assayed using the DuoSet Human Total HO-1/HMOX1 assay (R&D Systems DYC3776) according to the manufacturer's instructions.

Eight HO-1 standards were prepared in reagent diluent (0.5% Trition-X100 and 1 mM EDTA in PBS at pH 7.2) at concentrations ranging from 0.15625 to 10 ng/ml, including a negative control. The HO-1 capture antibody was diluted to a concentration of 8 µg/ml in PBS and was bound to the microtitre plate (Greiner Bio-One) overnight at room temperature. The unbound antibody was then removed by washing 3 times with wash buffer (0.05% Tween 20 in PBS) on an automatic plate washer. The plate was blocked with 300 µl per well of 1% bovine serum albumin (BSA) in PBS for 1 hour and washed 3 times in wash buffer. 100 µl of cell lysate, diluted ⅕, or standard was added to duplicate wells. The plate was incubated at room temperature for 2 hours before being washed three times with wash buffer. 100 µl of HO-1 detection antibody, diluted to a concentration of 200 ng/ml, was added to each well and the plate incubated at room temperature for 2 hours. The plate was washed as before. 100 µl of ½₀₀ diluted streptavidin horseradish peroxidase (HRP) was added to each well and incubated in the dark for 20 minutes at room temperature. The plate was washed as before and then 100 µl of substrate solution (R&D Systems DY999, 1:1 mixture of Colour Reagent A and Colour Reagent B) was added to each well and incubated, in the dark at room temperature, until colour developed (approx 20 minutes). 50 µl of stop solution (2M H2SO4) was applied to each well and the plate read on a microplate reader (Dynex MRX) at 450 nm with wavelength correction set at 540 nm.

A standard curve was plotted of mean OD versus HO-1 concentration and the line of best fit calculated by regression analysis. The unknown concentration of HO-1 protein in all the samples was calculated from this.

The results were normalised using the total protein data and expressed as ng HO-1 per µg protein.

The test compounds were sulforaphane, an NRF2 agonist, and 22(R)-hydroxycholesterol, a liver X receptor α/β agonist, and mixtures thereof.

Results

The results are summarised in Table 2 from which it is apparent that there was an up-regulation of hemoxygenase 1 protein in HaCaT immortalised human keratinocyte cells treated with a combination of 1 µM sulforaphane, an NRF2 agonist, and 10 µM 22(R)-hydroxycholesterol, a liver X receptor α/β agonist. Synergy was also observed with the combination of 0.05 µM sulforaphane and 10 µM 22(R)-hydroxycholesterol. Synergies were not seen with combinations of 0.01 µM sulforaphane and 10 µM 22(R)-hydroxycholesterol, 1 µM sulforaphane and 1 µM 22(R)-hydroxycholesterol, 0.05 µM sulforaphane and 1 µM 22(R)-hydroxycholesterol, and 0.01 µM sulforaphane and 1 µM 22(R)-hydroxycholesterol.

TABLE 2

HO-1 protein (ng HO-1 per µg protein) expressed from HaCaT cell treated with sulforaphane (NRF2 agonist) and 22(R)-hydroxycholesterol, a liver X receptor α/β agonist (n = 3).

| Test compounds | HO-1 protein (ng HO-1 per µg protein) |
| --- | --- |
| Ethanol + DMSO | 0.934 ± 0.382 |
| Ethanol | 1.285 ± 0.606 |
| DMSO | 1.602 ± 0.038 |
| 1 µM 22(R)-hydroxycholesterol | 1.486 ± 0.387 |
| 10 µM 22(R)-hydroxycholesterol | 3.174 ± 0.119 |
| 1 µM sulforaphane | 1.910 ± 0.418 |
| 0.05 µM sulforaphane | 1.600 ± 0.385 |
| 0.01 µM sulforaphane | 1.602 ± 0.248 |
| 1 µM 22(R)-hydroxycholesterol + 1 µM sulforaphane | 2.308 ± 0.383 |
| 1 µM 22(R)-hydroxycholesterol + 0.05 µM sulforaphane | 1.873 ± 0.278 |
| 1 µM 22(R)-hydroxycholesterol + 0.01 µM sulforaphane | 2.074 ± 0.151 |
| 10 µM 22(R)-hydroxycholesterol + 1 µM sulforaphane | 7.437 ± 0.035 |
| 10 µM 22(R)-hydroxycholesterol + 0.05 µM sulforaphane | 4.842 ± 1.018 |
| 10 µM 22(R)-hydroxycholesterol + 0.01 µM sulforaphane | 3.063 ± 0.573 |

Conclusions

Sulforaphane, an NRF2 agonist appears to synergistically up-regulate HO-1 protein in HaCaT immortalised human keratinocyte cells in combination with 22(R)-hydroxycholesterol, a liver X receptor α/β agonist.

Example 3

NADP(H): Quinone Oxidoreductase (NQO-1) Gene Expression Assays of Hair Follicles Cells Temporal or occipital human scalp skin was obtained from subjects undergoing face-lift or hair transplant surgery with informed consent and ethics approval. Anagen VI hair follicles were isolated and maintained according to the method described in Philpott et al (J. Cell Sci 97, 463-471 (1990)). Dhurat et al (Int J Trichology, 2(2), 96-100 (July-December 2010)) describe that anagen is conventionally divided into six stages, Anagen I-V (proanagen), when the hair shaft grows within the hair follicle, and Anagen VI (metanagen), when the tip of the hair shaft emerges from the hair follicle. Hair follicles were stabilised in RNAlater (for PCR). Five individual Anagen VI hair follicles were used for each culture condition/patient.

In order to evaluate the effect of Nrf2 agonists on hair follicles, test groups (n=4 donor subjects) received Nrf2 agonist (sulforaphane or tert-butyl hydroxyquinone (tBHQ)) for 24 hours and control groups (n=4 donor subjects) received dimethyl sulfoxide vehicle alone.

RNA was extracted using the Qiagen RNeasy Microkit (maximum 5 mg tissue per extraction).

100 ng RNA was reverse transcribed using the Invitrogen Cloned AMV First Strand Synthesis kit, according to manufacturers' instructions. TaqMan primer sets for HO-1 (Hs01110250_m1), NQO-1 (Hs00168547_m1) and Nrf2 (Hs00232352_m1) were obtained from the Invitrogen inventoried assays (Life technologies Ltd.).

cDNA was diluted 1:10 in RNase free water. Each reaction consisted of 1 µL 20× TaqMan assay, 10 µL Taqman Fast Advance Mastermix, 5 µL RNase free water and 2 ng of cDNA. Plates were run on an Applied Biosystems StepOnePlus™ Real Time PCR machine. Fast cycling conditions were used, utilising a 2 minute polymerase activation step at 95° C., followed by 45 cycles of denaturing at 95° C. for 1 second, and annealing/extension at 60° C. for 20 seconds.

All PCR reactions were normalised to the housekeeping control PPIA, which showed no variation between treatments. Data was analysed by the ΔΔCt methodology The test compounds were sulforaphane, an NRF2 agonist, and 22(R)-hydroxycholesterol, a liver X receptor α/β agonist, and mixtures thereof.

Results

Results are presented in Table 3 which shows NQO-1 gene expression (fold change compared to 18S) in hair follicles treated with sulforaphane and 22(R)-hydroxycholesterol. Significant (p≤0.01) up-regulation of NQO-1 mRNA in human hair follicle cells treated with 10 μM sulforaphane and 5 μM 22(R)-hydroxycholesterol was observed compared to the next most effective NQO-1 agonist which was 10 μM sulforaphane.

TABLE 3

NQO-1 gene expression (fold change compared to 18S) of hair follicle cells after 24 hour treatment with either sulforaphane or 22(R)-hydroxycholesterol or a combination thereof. P-values relates to significance of sulforaphane or tBHQ to vehicle control at 95% confidence limits (n = 3).

| | NQO-1 Fold change compared to 18S |
|---|---|
| Vehicle | 1.01 ± 0.04 |
| 10 μM sulforaphane | 5.44 ± 0.50 |
| 5 μM 22(R)-hydroxycholesterol | 1.04 ± 0.05 |
| 10 μM sulforaphane + 5 μM 22(R)-hydroxycholesterol | 6.77 ± 0.48 |

Conclusion

Sulforaphane, an NRF2 agonist appears to synergistically up-regulate NQO-1 protein in human hair follicle cells in combination with 22(R)-hydroxycholesterol, a liver X receptor α/β agonist.

Example 4

Immunohistochemical Analysis of NADP(H): Quinone Oxidoreductase (NQO-1) in Hair Follicles Scalp biopsies (4 mm) were obtained from patients following ethical approval and informed patient consent (Intertek CRS, Manchester, UK). Immunohistochemical staining of NQO-1 protein expression and localisation was performed on 6 μm scalp cryosections. Briefly, cryosections were fixed in acetone before permeabilisation in 0.1% Triton X 100 (an octyl phenol ethoxylate). Washes were performed in phosphate- or tris-buffered saline (PBS, TBS). The primary antibody (1:100 Anti-NQO-1 antibody [A180] (ab28947; Abcam, Cambridge, UK)) was incubated overnight at 4° C. before incubation with the secondary antibody (1:200; Alexafluor®488 Donkey anti-mouse IgG (H+L) antibody (A-21202; Life Technologies, Paisley, UK)) for 60 minutes. Imaging of immunolocalisation was performed using a Zeiss LSM confocal microscope.

Results

Figure 2:
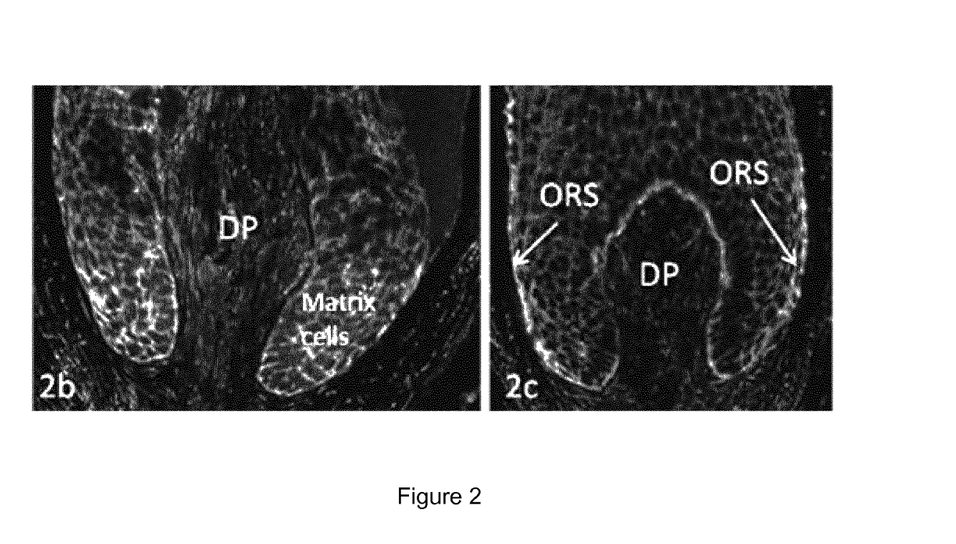
FIG. 2 which shows localisation of NQO-1 protein expression in human hair follicles by indirect immunofluorescence within the matrix region of the hair bulb (2b) and in the outer root sheath (ORS) of the hair follicle bulb region (2c) (DP is the dermal papilla).

The results are shown in FIG. 2 which shows localisation of NQO-1 protein expression in human hair follicles by indirect immunofluorescence. Positive staining for NQO-1 (in white) was observed particularly within the matrix region of the hair bulb (2b) and in the outer root sheath (ORS) of the hair follicle bulb region (2c). In FIG. 2, DP is the dermal papilla.

Conclusions

Immunohistochemical analysis of NADP(H): quinone oxidoreductase (NQO-1) in hair follicles demonstrates that NQO-1 was observed particularly within the matrix region of the hair bulb and in the outer root sheath of the hair follicle bulb region.

The invention claimed is:

1. An oral or topical composition comprising a nuclear factor erythroid-2 related factor 2 agonist and a liver X receptor agonist, wherein the amounts of each of the nuclear factor erythroid-2 related factor 2 agonist and the liver X receptor agonist produce a synergistic benefit of hair fibre growth, wherein the oral or topical composition comprises ≤9% w/w β-sitosterol, and wherein the nuclear factor erythroid-2 related factor 2 agonist comprises granilin and the liver X receptor agonist comprises a compound selected from the group consisting of 22(R)-hydroxycholesterol, 3-[3-[[[2-chloro-3-(trifluoromethyl)phenyl]methyl](2,2-diphenylethyl)amino]propoxy]benzeneacetic acid hydrochloride (GW 3965) and/or salts thereof, and stigmasterol; or wherein the nuclear factor erythroid-2 related factor 2 agonist comprises 1 μM sulforaphane and the liver X receptor agonist comprises 10 μM 22(R)-hydroxycholesterol, and wherein when the oral or topical composition comprises a catechin, the oral or topical composition comprises 0.001 to 90% w/w catechins, and wherein the oral or topical composition excludes pregnenolone, 4, 5-dihydrofuranodiene-6-one, epoxy santamarin, hydroquinone, longistyline, monacolin K, protoanemonin, N-(2,2,2-trifluoro-ethyl)-N-[4-(2,2,2-trifluoro-1-hydroxy-1-trifluoromethyl-ethyl)-phenyl]-benzenesulfonamide, dihydronepetalactone, iridomyrmecin, and dihydroactinidiolide, and wherein when the oral or topical composition comprises guggelsterone and epigallocatechin gallate, the oral or topical composition excludes a guggelsterone to epigallocatechin gallate weight ratio of 1 to 28, and wherein when the oral or topical composition comprises sodium dilauramide glutamide lysine, the oral or topical composition excludes 0.3% w/w sodium dilauramide glutamide lysine.

2. An oral or topical composition comprising a nuclear factor erythroid-2 related factor 2 agonist and a liver X receptor agonist, wherein the amounts of each of the nuclear factor erythroid-2 related factor 2 agonist and the liver X receptor agonist produce a synergistic induction of the antioxidant response element and/or up-regulation of hemoxygenase 1 in HaCaT immortalised human keratinocyte cells and/or up-regulation of NAD(P)H dehydrogenase (quinone) 1 in human hair follicle cells, wherein the oral or topical composition comprises ≤9% w/w β-sitosterol, and wherein the nuclear factor erythroid-2 related factor 2 agonist comprises granilin and the liver X receptor agonist comprises a compound selected from the group consisting of 22(R)-hydroxycholesterol, 3-[3-[[[2-chloro-3-(trifluoromethyl)phenyl]methyl](2,2-diphenylethyl)amino]propoxy]benzeneacetic acid hydrochloride (GW 3965) and/or salts thereof, and stigmasterol;

or wherein the nuclear factor erythyroid-2 related factor 2 agonist comprises 1 μM sulforaphane and the liver X receptor agonist comprises 10 μM 22(R)-hydroxycholesterol, and wherein when the oral or topical composition comprises a catechin, the oral or topical composition comprises 0.001 to 90% w/w catechins, and wherein the oral or topical composition excludes pregnenolone, 4, 5-dihydrofuranodiene-6-one, epoxy santamarin, hydroquinone, longistyline, monacolin K, protoanemonin, N-(2,2,2-trifluoro-ethyl)-N-[4-(2,2,2-trifluoro-1-hydroxy-1-trifluoromethyl-ethyl)-phenyl]-benzenesulfonamide, dihydronepetalactone, iridomyrmecin, and dihydroactinidiolide, and wherein when the oral or topical composition comprises guggelsterone to epigallocatechin gallate, the oral or topical composition excludes a guggelsterone to epigallocatechin gallate weight ratio of 1 to 28, and wherein when the oral or topical composition comprises sodium dilauramide glutamide lysine, the oral or topical composition excludes 0.3% w/w sodium dilauramide glutamide lysine.

3. A method of promoting hair fibre growth comprising applying to hair fibres and/or scalp the oral or topical composition according to claim 1.

4. A method of inducing antioxidant response element and/or up-regulation of hemoxygenase 1 in HaCaT immortalised human keratinocyte cells and/or up-regulation of NAD(P)H dehydrogenase (quinone) 1 in human hair follicle cells comprising treating the cells with an oral or topical composition according to claim 2.

5. An oral or topical composition according to claim 1, wherein the oral or topical composition comprises ≤8% w/w β-sitosterol.

6. An oral or topical composition according to claim 1, wherein the oral or topical composition comprises 0.005 to 70% w/w catechins.

7. An oral or topical composition according to claim 1, wherein the oral or topical composition comprises 0.01 to 50% w/w catechins.

8. An oral or topical composition according to claim 2, wherein the oral or topical composition comprises ≤8% w/w β-sitosterol.

9. An oral or topical composition according to claim 2, wherein the oral or topical composition comprises 0.005 to 70% w/w catechins.

10. An oral or topical composition according to claim 2, wherein the oral or topical composition comprises 0.01 to 50% w/w catechins.

* * * * *